United States Patent
Gagnon et al.

(10) Patent No.: US 8,660,636 B2
(45) Date of Patent: Feb. 25, 2014

(54) REGIONAL RECONSTRUCTION AND QUANTITATIVE ASSESSMENT IN LIST MODE PET IMAGING

(75) Inventors: Daniel Gagnon, Twinsburg, OH (US); Piotr J. Maniawski, Chagrin Falls, OH (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/145,115

(22) PCT Filed: Dec. 23, 2009

(86) PCT No.: PCT/IB2009/055948
§ 371 (c)(1),
(2), (4) Date: Dec. 8, 2011

(87) PCT Pub. No.: WO2010/082101
PCT Pub. Date: Jul. 22, 2010

(65) Prior Publication Data
US 2012/0089015 A1    Apr. 12, 2012

Related U.S. Application Data

(60) Provisional application No. 61/145,590, filed on Jan. 19, 2009.

(51) Int. Cl.
*A61B 5/00* (2006.01)
(52) U.S. Cl.
USPC ............................ 600/425; 600/407; 600/436
(58) Field of Classification Search
None
See application file for complete search history.

(56) References Cited

U.S. PATENT DOCUMENTS

| | | | | |
|---|---|---|---|---|
| 7,221,728 B2 * | 5/2007 | Edic et al. | ........................... | 378/8 |
| 7,734,119 B2 * | 6/2010 | Cheryauka et al. | ........... | 382/302 |
| 7,907,772 B2 * | 3/2011 | Wang et al. | .................... | 382/154 |
| 2007/0118100 A1 * | 5/2007 | Mahesh et al. | ................... | 606/32 |
| 2007/0237295 A1 * | 10/2007 | Gundel | ........................... | 378/62 |
| 2010/0142775 A1 * | 6/2010 | Ganeshan et al. | ............. | 382/128 |

FOREIGN PATENT DOCUMENTS

WO    WO 2007100955 A2 *    9/2007
WO           2008146186 A2        12/2008

OTHER PUBLICATIONS

Ziegler, A., et al.; Iterative reconstruction of a region of interest for transmission tomography; 2008; Med. Phys.; 35 (4)1317-1327.

* cited by examiner

*Primary Examiner* — Peter Luong

(57) ABSTRACT

A method for reconstructing list mode data comprises: reconstructing all list mode data of a list mode data set (30, 160) to generate a first reconstructed image (32, 62); selecting a sub-set of the list mode data set; and reconstructing the sub-set of the list mode data set to generate an enhanced reconstructed image (84, 86). An image generation system comprises: a reconstruction module (24) configured to perform a standard reconstruction of a list mode data set to generate a standard reconstructed image (32, 62); and a re-reconstruction module (24, 70, 80, 82, 150, 152, 154) configured to perform a reconstruction other than the standard reconstruction of at least a portion of the list mode data set to generate an enhanced reconstructed image (84, 86).

15 Claims, 2 Drawing Sheets

REGIONAL RECONSTRUCTION AND QUANTITATIVE ASSESSMENT IN LIST MODE PET IMAGING

CROSS REFERENCE TO RELATED APPLICATIONS

Figure 1:
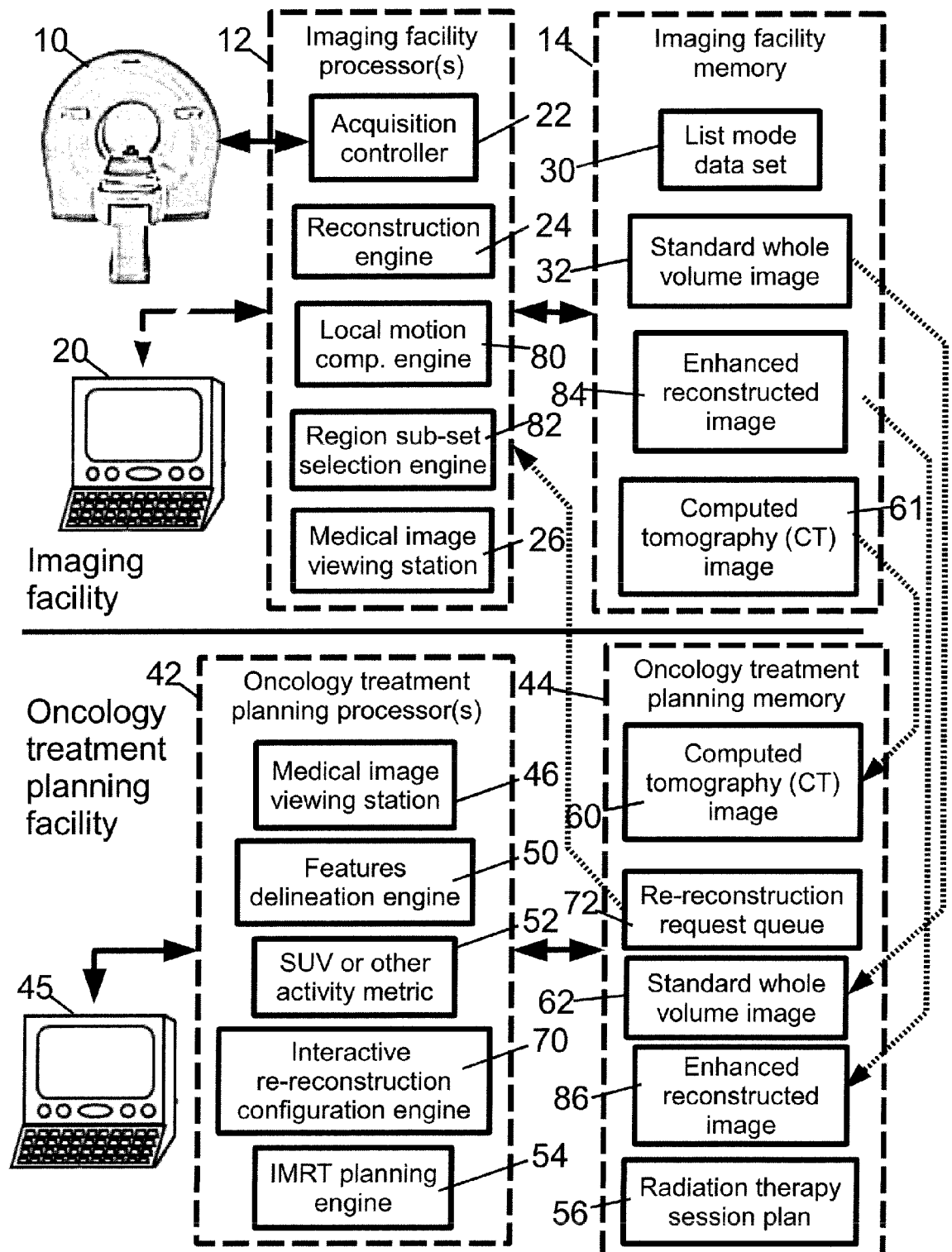

This application claims the benefit of U.S. provisional application Ser. No. 61/145,590 filed Jan. 19, 2009, which is incorporated herein by reference.

The following relates to the medical arts, medical imaging arts, medical diagnostic arts, positron emission tomography (PET) imaging arts, single photon emission computed tomography (SPECT) arts, and related arts.

The use of positron emission tomography (PET), single photon emission computed tomography (SPECT), and other imaging modalities in oncological diagnosis, assessment, and treatment planning is increasing. PET and SPECT entail administering a radiopharmaceutical to the subject (for example, a human or animal subject) and detecting radiation emitted from the subject by the radiopharmaceutical. The radiopharmaceutical may be tailored to preferentially collect in the bloodstream or in other anatomical regions of interest so as to provide image contrast for those regions. PET and SPECT are recognized as complementary to transmission computed tomography (CT) for oncology, because PET and SPECT tend to provide functional information relating to tumor metabolism, growth, and necrosis, whereas CT provides primarily structural information.

The acquisition of PET and SPECT imaging data is complicated by the use of a radiopharmaceutical. Consideration for subject safety, often reinforced by applicable government regulations, dictates the use of relatively low radiopharmaceutical dosages. This, in turn, translates into low radioactivity "count rates" and consequently slow data acquisition. A typical PET imaging session, for example, can extend over a half hour or longer. The scheduling and execution of a PET imaging session is a substantial undertaking, and is usually conducted at a dedicated radiological imaging facility by a suitably trained radiological specialist. The PET imaging session encompasses the imaging data acquisition and the conversion of the acquired radioactivity "counts" into an image via a process known in the art as "image reconstruction".

The reconstruction process is computationally intensive. Two general classes of reconstruction algorithms or "engines" are in common use: non-iterative "analytical" algorithms that directly compute the reconstructed image from the acquired PET or SPECT data; and iterative algorithms that iteratively adjust a reconstructed image to approximate the acquired PET or SPECT data. Analytical reconstruction algorithms include filtered back-projection and Fourier reprojection techniques, and are mathematical transforms that typically preserve all information content contained in the acquired data. However, analytical methods also retain all noise content, and accordingly images generated by analytical methods can be difficult to interpret. Filtering or smoothing can sometimes improve the analytical image. On the other hand, the iterative algorithms, which include maximum likelihood-expectation maximization (ML-EM) and its variants, are generally more robust against noise. However, iterative reconstruction algorithms have certain practical convergence issues, and for a given image it is not simple to predict how many iterations will be required. Additionally, iterative reconstruction algorithms do not retain all information content contained in the acquired data.

In addition to the choice of algorithm employed by the reconstruction engine, the reconstructed image can also be affected by factors such as the parameters used in the reconstruction (such as the spatial resolution or voxel size), the selection of acquired PET or SPECT data that are input to the reconstruction engine, and by any preprocessing that may be applied to that data. For example, Busch et al., WO 2007/100955 (published 7 Sep. 2007) which is incorporated herein by reference in its entirety describes local motion compensation (LMC) preprocessing to correct for motion of a local feature (such as a beating heart, for example). These various factors can impact both image quality and speed of image reconstruction.

The complexity of the image reconstruction process translates into a wide variety of information, and information quality, that is attainable from a given acquired PET or SPECT data set. Depending upon the selection of reconstruction algorithm, the selection of data undergoing reconstruction, the selection of reconstruction parameters, LMC or other data preprocessing, or so forth, the resulting image can range anywhere from almost useless to highly probative of a cancerous tumor or other feature of interest.

Unfortunately, existing oncological imaging paradigms do not effectively leverage information contained in the acquired SPECT or PET data. The physician, radiation therapist, or other oncological specialist has limited interaction with the imaging facility and imaging specialists. In a typical oncology environment, the oncological specialist schedules a PET or SPECT imaging session, and receives the reconstructed PET or SPECT image in a standardized format, such as in the form of a standard "4 mm$^3$" reconstructed PET image having cubic pixels that are 4 mm on a side. The oncological specialist views this standard image at an imaging workstation (which may be a suitably programmed general-purpose computer, or a dedicated image viewing workstation) using software that extracts slices, formulates three-dimensional renderings, or otherwise presents human-viewable representations of the standard image or portions thereof.

In a typical radiation therapy workflow, for example, the oncological specialist uses CT images to delineate a cancerous tumor and neighboring "critical structures" such as neighboring radiation-sensitive organs. An intensity modulated radiation therapy (IMRT) plan is generated based on the delineated features, and is applied using a linear accelerator ("linac") or other radiation therapy system. PET or SPECT images are generally used as supplementary data, to provide functional information such as standardized uptake value (SUV), assess any observable necrosis or metastasis, and so forth. PET and SPECT can sometimes be superior to CT for detection tasks such as detecting an initial malignant tumor or lesion or detecting the presence and rate of metastasis of the cancer, because the functional sensitivity of PET can cause nascent tumors or lesions to appear as bright spots reflecting high local metabolism.

The reconstruction of the entire PET or SPECT data set into a "standard" image, such as a 4 mm$^3$ standard PET image, is efficient for detection tasks, which do not require detailed analysis of the detected features. Generating the standard reconstruction is efficient, because it is a standardized task and uses standard reconstruction parameters. The entire data set is used, which provides reassurance that all information content is preserved, and the parameters of the standard reconstruction are, on average, good parameters for the reconstruction. Still further, the standard reconstruction is familiar to the oncological specialist—it is what the oncological specialist "expects" to receive.

However, the standard reconstruction, such as the 4 mm$^3$ standard PET image, may be less than ideal for more advanced tasks such as SUV assessment, high resolution analyses, or so forth. Advanced preprocessing such as LMC or region selection call for additional information that may be unavailable to the imaging specialist during the initial imaging session. Still further, computationally intensive preprocessing or computationally intensive reconstruction algorithms that may in some instances improve the image quality may be too costly to apply to the complete data set.

The following provides new and improved apparatuses and methods which overcome the above-referenced problems and others.

In accordance with one disclosed aspect, a method is disclosed for reconstructing list mode data, the method comprising: reconstructing all list mode data of a list mode data set to generate a first reconstructed image; selecting a sub-set of the list mode data set; and reconstructing the sub-set of the list mode data set to generate an enhanced reconstructed image.

In accordance with another disclosed aspect, an image generation system is disclosed, comprising: a reconstruction module configured to perform a standard reconstruction of a list mode data set to generate a standard reconstructed image; and a re-reconstruction module configured to perform a reconstruction other than the standard reconstruction of at least a portion of the list mode data set to generate an enhanced reconstructed image.

In accordance with another disclosed aspect, an image generation method is disclosed, comprising: reconstructing an image from image data; transferring the image to a treatment planning facility; at the treatment planning facility, selecting one or more parameters for a re-reconstruction that are different from parameters used in the initial reconstruction; and re-reconstructing an updated image from at least a portion of the image data using the selected one or more parameters for the re-reconstruction.

One advantage resides in facilitating obtaining more complete information from list mode imaging data.

Another advantage resides in more efficient use of information contained in list mode imaging data.

Another advantage resides in providing increased flexibility and capability to oncological specialists in utilizing list mode imaging data.

Further advantages will be apparent to those of ordinary skill in the art upon reading and understand the following detailed description.

FIG. 1 diagrammatically illustrates a medical imaging facility and an oncological treatment planning facility including an indication of interactions between the imaging facility and the oncological treatment planning facility.

Figure 2:
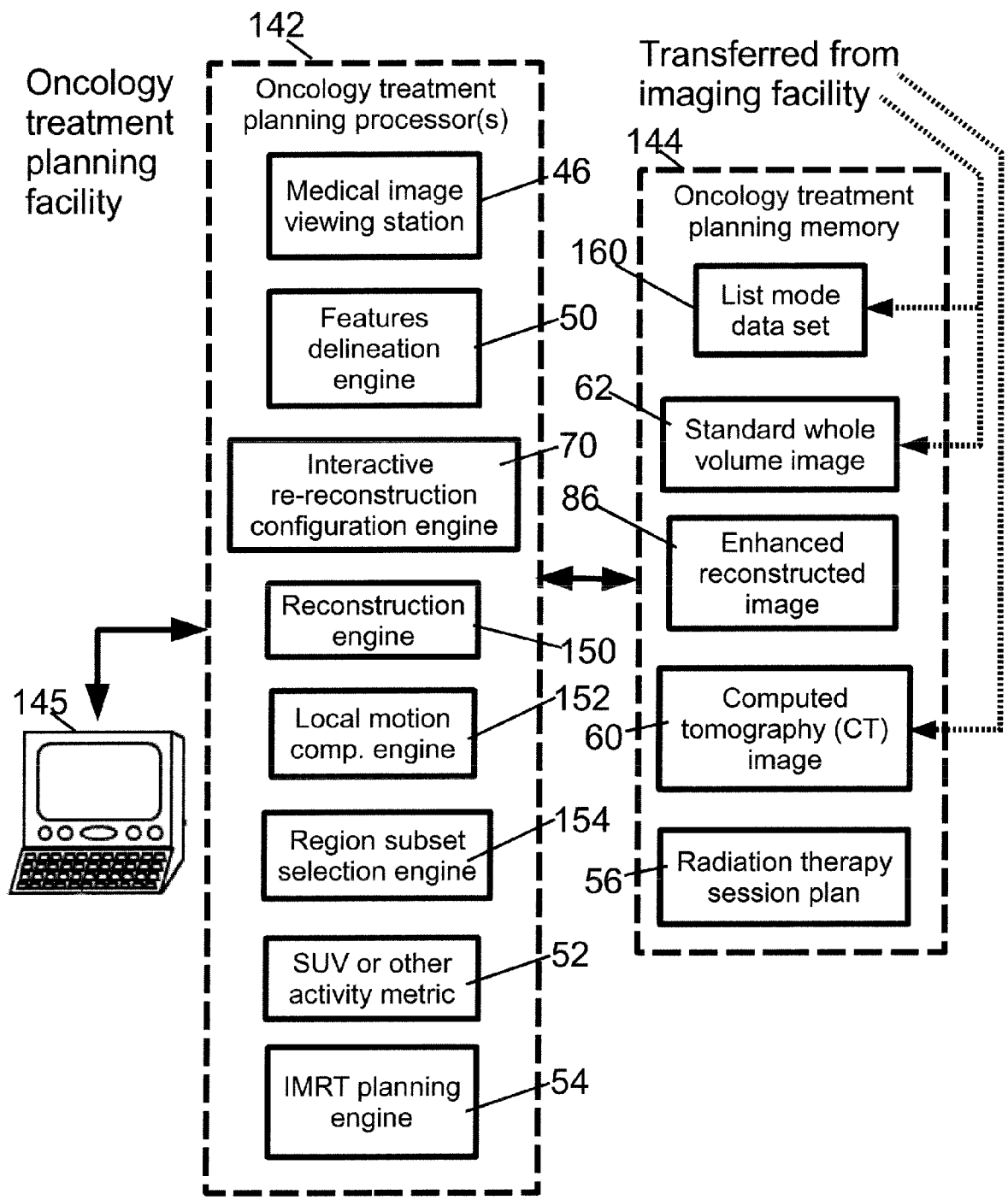

FIG. 2 diagrammatically illustrates an oncological treatment planning facility that includes independent list mode imaging data reconstruction capability.

It is recognized herein that existing oncological treatment workflows do not efficiently utilize the functional sensitivity of PET and SPECT for quantitative analyses. On the other hand, it is also recognized herein that existing oncological treatment workflows have substantial advantages as employed for detection of cancerous tumors and lesions and for detecting and monitoring metastatic cancer. The following discloses improved oncological imaging paradigms that retain these existing advantages for detection while providing enhanced capabilities for quantitative analyses.

With reference to FIG. 1, a medical imaging system includes one or more medical imaging instruments 10, one or more imaging facility processors 12, and one or more imaging facility memories 14. The one or more imaging instruments 10 include at least one nuclear medical imaging instrument, such as a positron emission tomography (PET) imaging instrument for acquiring PET data or a gamma camera for acquiring single photon emission computed tomography (SPECT) data. Optionally, the one or more medical imaging instruments 10 include other modalities, such as a magnetic resonance (MR) imaging instrument, a transmission computed tomography (CT) imaging instrument, or so forth. In some embodiments, the one or more medical imaging instruments 10 include a hybrid imaging apparatus that provides two or more imaging modalities. For example, the one or more medical imaging instruments 10 optionally include a hybrid PET/CT imaging instrument such as a Gemini™ PET/CT system available from Koninklijke Philips Electronics N.V. (Eindhoven, The Netherlands) or a hybrid SPECT/CT imaging instrument such as a Brightview™, Precedence™, or SKYlight™ SPECT/CT system available from Koninklijke Philips Electronics N.V. (Eindhoven, The Netherlands). Other commercial or non-commercial standalone and/or hybrid systems are also contemplated, such as a hybrid PET/MR system. The one or more medical imaging instruments 10 may be housed in a single room, or in two or more rooms of the medical imaging facility, which may be a dedicated imaging facility or a component of a larger medical entity such as a hospital.

The one or more imaging facility processors 12 may be suitably embodied, for example, by one or more computers 20, which may be one or more personal computers, laptop or notebook computers, and/or one or more remote digital processors such as one or more Internet-based servers that are accessed via a personal computer, netbook, "dumb terminal," or other network-capable user interfacing device. The one or more imaging facility processors 12 define and perform various imaging facility components, such as defining one or more acquisition controllers 22 for controlling the one or more imaging systems 10 to generate imaging data, defining one or more reconstruction engines 24 for performing reconstruction of acquired imaging data, and defining together with a display and user interface devices of the one or more computers 20 a medical image viewing station 26. The one or more imaging facility memories 14 can include one or more magnetic storage media, one or more optical storage media, one or more electrostatic storage media, or so forth. Some illustrative examples include: a hard disk or other internal storage device or devices of the one or more computers 20; an external hard drive; a redundant array of independent disks (RAID) system; a remote Internet storage facility; or so forth. The one or more imaging facility memories 14 may also include or have access to a picture archive and communication system (PACS) maintained by a hospital or other organization owning or associated with the medical imaging facility.

In a typical task involving SPECT or PET imaging, the relevant acquisition controller 22 operates the SPECT or PET imaging system of the one or more medical imaging instruments 10 to generate a list mode imaging data set 30 that is stored in the one or more medical imaging facility memories 14. The term "list mode data set" and similar terminology as used herein denotes a set of nuclear medical imaging data that retains all information about the radiation detection events. This information includes: energy information at least sufficient to determine that the radiation detection event corresponds to a particle of interest such as a 511 keV gamma ray in the case of PET, or a particle of energy consonant with the radiopharmaceutical used in a SPECT imaging session; time information; and location information (for example, stored as information identifying the radiation detector, or information on the spatial location of the detection event). For SPECT, each particle detection event corresponds to a line or plane of response defined by the geometry of the radiation detector (or, by the geometry of a radiation collimator associated with the radiation detector). For PET, a pair of substantially simultaneous 511 keV gamma particle detection events define a line of response connecting the substantially simultaneous 511 keV gamma particle detection events. In some embodiments, time of flight information is also stored, in which case a time difference between the substantially simultaneous 511 keV gamma particle detection events is used to further localize the positron-electron annihilation event along the line of response. It will be appreciated that the energy, time, and location information can be stored in various ways, and the term "list mode" is intended to encompass any format for storing this information. In some embodiments, the energy information is not quantitatively stored, but rather the energy information is stored implicitly by storing information pertaining only to radiation detection events that fall within a suitable energy window, such as an energy window at about 511 keV in the case of PET list mode data.

The list mode data set 30 is reconstructed using the reconstruction engine 24 to generate a standard whole volume image 32, that is, a first reconstructed image, which is reconstructed from the complete list mode data set 30 using standard reconstruction parameters. For example, in the case of PET imaging data a typical standard is to reconstruct a whole volume image with a 4 $mm^3$ spatial resolution. More generally, the standard whole volume image 32 employs standard reconstruction parameters that are a standard for the imaging facility, so that a human imaging specialist can initiate the reconstruction without manual configuration beyond identifying the list mode data set 30 and, possibly, selecting the standard reconstruction algorithm. In some embodiments, the list mode data set 30 is reconstructed using the reconstruction engine 24 to generate the standard whole volume image 32 in an automatic fashion, without the intervention of a human imaging specialist. The standard reconstruction can employ substantially any suitable iterative reconstruction algorithm such as maximum likelihood-expectation maximization (ML-EM) or a variant thereof, or can employ substantially any suitable noniterative analytical reconstruction algorithm such as a filtered back-projection algorithm or a Fourier reprojection algorithm. Because the standard reconstruction algorithm is used, the standard whole volume image 32 is generated without input from any oncological specialist, which advantageously enhances efficiency but also results in the standard whole volume image 32 not being tailored or customized for any particular analytical purpose or targeted to any particular imaged feature such as a malignant tumor or the like.

FIG. 1 also depicts in diagrammatic fashion an oncological treatment planning facility, which is associated with the medical imaging facility in a suitable fashion. For example, in some embodiments the medical imaging facility and the oncological treatment planning facility are departments or other operational units of a hospital or other medical system, while in other embodiments the oncological treatment planning facility contracts with the medical imaging facility for the latter to provide medical images to the former. Other suitable associations are also contemplated, such as the medical imaging facility being a division or other unit of the oncological treatment planning facility, or vice versa. Additionally, the facilities depicted in FIG. 1 may encompass other functionality. For example, the oncological treatment planning facility may be an oncological planning and treatment facility that both plans and executes oncological treatments. As another example, the imaging facility may be a component of a radiology department that additionally performs radiation therapy treatments.

The illustrative oncological treatment facility includes a one or more oncological treatment planning processors 42, and one or more imaging facility memories 44. The one or more oncology treatment planning processors 42 may be suitably embodied, for example, by one or more computers 45, which may be one or more personal computers, laptop or notebook computers, and/or one or more remote digital processors such as one or more Internet-based servers that are accessed via a personal computer, netbook, "dumb terminal," or other network-capable user interfacing device. The one or more imaging facility memories 44 can include one or more magnetic storage media, one or more optical storage media, one or more electrostatic storage media, or so forth. Some illustrative examples include: a hard disk or other internal storage device or devices of the one or more computers 45; an external hard drive; a redundant array of independent disks (RAID) system; a remote Internet storage facility; or so forth. The one or more imaging facility memories 44 may also include or have access to a picture archive and communication system (PACS) maintained by a hospital or other organization owning or associated with the medical imaging facility.

The one or more oncology treatment planning processors 42 define and perform various oncology treatment planning components, such as defining together with a display and user interface devices of the one or more computers 45 a medical image viewing station 46 via which an oncological specialist can view and navigate through the standard whole volume image 32. The one or more oncology treatment planning processors 42 further define: an optional features delineation engine 50 for delineating features such as a cancerous tumor or lesion, neighboring radiation-sensitive organs, or so forth; an optional quantitative diagnostic analyzer 52 such as an activity metric (e.g., a standardized uptake value or SUV analysis); and an optional intensity modulated radiation therapy (IMRT) planning engine 54. The features delineation engine can operate in a manual, automatic, or semiautomatic fashion. For example, in a manual embodiment the oncological specialist employs a graphical user interface (GUI) component of the viewing station 46 to lasso, rope, outline, or otherwise manually delineate features of interest. In an automatic embodiment, automatic intensity thresholding can be used to segment the image based on voxel intensities to delineate features of interest. One example of a semi-automatic delineation approach employs lassoing to approximately delineate a region, followed by automatic intensity thresholding to adjust the approximate manual delineation, followed optionally by further manual adjustments. The IMRT planning engine 54 uses known techniques to optimize intensity modulation parameters of a radiation therapy system, such as leaflet collimator settings, beam intensity settings, or the like, to generate a radiation therapy session plan providing a desired integrated radiation dosage profile in the subject. The output of the IMRT planning engine 54 is a radiation therapy session plan 56 that is suitably stored in the one or more oncology therapy planning memories 44.

For the purpose of delineating structures, it is sometimes preferred to employ a transmission computed tomography (CT) image 60 of the subject, which is suitably stored in the one or more oncology therapy planning memories 44. The CT image 60 may be generated by a CT imaging instrument of the one or more medical imaging instruments 10 of the illustrated imaging facility, in which case the reconstructed CT image 61 is suitably first stored in the imaging facility memory or memories 14 and then transferred to the oncological treatment planning memory or memories 44. Alternatively, the CT image 60 may be generated by another imaging facility or by a CT imaging instrument in the possession of the oncology treatment planning facility (alternatives not illustrated).

The PET or SPECT images, on the other hand, are generally used for tumor or lesion detection, and/or to analyze functional aspects of the malignancy. Toward this end, the standard whole volume PET or SPECT image 32 is transferred (for example, via the Internet, or via a wired, wireless, or hybrid hospital digital network, or via a physically transported digital data storage medium such as an optical disk, or so forth) from the imaging facility to the oncology treatment planning facility where a copy of the standard whole volume image 62 is suitably stored in the oncological treatment planning memory or memories 44. The oncological specialist can then employ the medical image viewing station 46 at the oncological treatment planning facility to view the standard whole volume image 32 or selected portions (e.g., slices) or renderings thereof. The standard whole volume image 32 is typically well-suited for detecting cancerous tumors or lesions, and provides some indication of the general level of metabolic activity, which can optionally be quantified using the optional quantitative diagnostic analyzer 52. However, the image reconstruction that generated the standard whole volume image 32 was not in general optimized to provide the best image quality characteristics for a particular tumor or lesion. For example, a common standard PET reconstruction employs 4 $mm^3$ voxels—this resolution may be too coarse for detailed determination of the shape or activity of a small tumor or lesion. If the tumor or lesion is located in a lung or other cyclically moving organ, or is at a location that is influenced by (e.g., moved due to contact with or proximity to) a cyclically moving organ, then the representation of the tumor or lesion in the standard whole volume image 32 will be blurred due to the motion. As a consequence, the standard whole volume image 32 may provide a less-than-ideal representation of a tumor or lesion identified by the oncological specialist in the standard whole volume image 32.

On the other hand, the acquisition of the list mode data set 30 typically takes a relatively long time, for example a half hour or longer for some PET scans and comparable times for SPECT scans. Operation of a PET or SPECT imaging instrument is also costly in terms of consumables (electricity, radiopharmaceutical, and so forth) and in terms of human time (the imaging specialist's time as well as the subject's time, in the case of a human subject). Moreover, administering the radiopharmaceutical to the subject amounts to exposing the subject to a certain radiation dosage, albeit at a level that is deemed safe by oncological profession and by any relevant government regulatory entities. As a consequence, it is desirable to limit the number of PET or SPECT imaging sessions as much as practicable, and it is undesirable to perform another PET or SPECT data acquisition in order to focus on an identified tumor or lesion.

Advantageously, the list mode imaging data set 30 that is stored in the one or more medical imaging facility memories 14 retains all information contained in the originally acquired imaging data. As a result, it is unnecessary to acquire a new data set. Rather, it is sufficient to redefine or refine the reconstruction process, and to perform a "re-reconstruction" using one or more of: (i) improved reconstruction parameters; (ii) selected preprocessing such as local motion compensation (LMC); and (iii) a selected sub-set of the list mode imaging data set 30, so as to produce an enhanced reconstructed image providing an enhanced representation of the tumor or lesion of interest.

Toward this end, with continuing reference to FIG. 1 the one or more oncological treatment planning processors 42 further define an interactive re-reconstruction configuration engine 70 that enables the oncological specialist to configure a re-reconstruction process. The oncological specialist is not necessarily well-trained in detailed aspects of imaging including image reconstruction. The interactive re-reconstruction configuration engine 70 enables the oncological specialist to specify parameters for a refined or enhanced reconstruction without resort to the lower-level terminology or concepts of the imaging technology. For example, the oncological specialist optionally identifies a region of interest in image space for reconstruction, but does not attempt to identify which list mode data of the list mode data set 30 contribute to image content of the region of interest in space. Thus, the oncological specialist can, in some embodiments, simply provide the delineation of the tumor or lesion of interest determined using the features delineation engine 50, or can graphically define a rectangular box containing the tumor or lesion of interest, so as to define a region of interest in image space for reconstruction. In some embodiments, the oncological specialist can use a mouse pointer or other graphical selection device to identify (i) a feature that is believed to be cyclically moving and (ii) a region that is believed to be substantially stationary respective to the cyclical motion, and then select to perform local motion compensation (LMC) for the cyclically moving feature. The oncological specialist can also in some embodiments optionally specify reconstruction parameters for the re-reconstruction, such as image space resolution. Typically, a higher resolution is requested for the re-reconstruction as compared with the standard reconstruction, although a lower resolution may also be requested, for example to reduce the signal to noise ratio (SNR). Still further, the oncological specialist may in some embodiments optionally request a quantitative diagnostic analysis be performed on a feature in the enhanced reconstructed image, such as an SUV analysis of a region believed to be a malignant tumor or lesion. Although the oncological specialist is not typically expected to be an expert in image reconstruction, the interactive re-reconstruction configuration engine 70 optionally also enables the oncological specialists to specify more advanced reconstruction parameters such as the type of reconstruction algorithm (for example, selecting from among filtered backprojection or iterative ML-EM reconstruction). These more advanced reconstruction parameters can be presented either as advanced settings of the re-reconstruction configuration for use by oncological specialists having requisite understanding of the reconstruction process, or alternatively or additionally can be presented in more intuitive terms. For example, a choice of reconstruction algorithm optionally may be presented as the options of: "reconstruct with more robustness against noise (iterative ML-EM)" or "reconstruct with no loss of information or noise content (filtered backprojection)". The latter selection optionally may also include check-boxes or another selection mechanism for selecting whether a partial volume correction or point spread function (PSF) correction is to be applied, optionally with suitable explanatory text informing the oncological specialist of the likely effect of these filters on image characteristics.

The re-reconstruction parameters (including settings such as image space resolution, reconstruction algorithm selection, the selection of optional LMC or other preprocessing, partial volume or PSF filters, and so forth) is suitably stored in a re-reconstruction request queue 72 of the one or more oncology treatment planning facility memories 44, and the queued re-reconstruction request is forwarded to the imaging facility via the Internet, a wired, wireless, or hybrid local area network, or so forth.

At the imaging facility, the re-reconstruction request is processed in a manual, automatic, or semi-automatic fashion. In a manual approach, a human imaging specialist reviews the re-reconstruction request, optionally consults with the oncology specialist if appropriate (for example, if there is ambiguity in the re-reconstruction request), and constructs a suitable reconstruction process to generate an enhanced reconstructed image in accordance with the re-reconstruction request. For example, the imaging specialist may program the reconstruction engine 24 to use the desired reconstruction algorithm (e.g., filtered backprojection or iterative ML-EM or another requested reconstruction algorithm) and to employ the requested spatial resolution or other reconstruction configuration parameters, and to invoke an optional local motion compensation (LMC) engine 80 optionally defined by the imaging facility processor or processors 12 to perform requested LMC preprocessing of the list mode data. If the re-reconstruction request includes a selection of a region of interest in image space for re-reconstruction, then the imaging specialist can select a suitable sub-set of the list mode data set for re-reconstruction. To do so, the imaging specialist starts with the region of interest in image space defined by the oncology specialist, and optionally employs a rectangular containment box to refine the region of image space for reconstruction (for example, to ensure that the region of image space for reconstruction comports with a required or computationally preferred rectangular geometry, or to ensure that the region of image space for reconstruction is larger than the tumor or other feature of interest, or so forth). The imaging specialist then invokes an optional region sub-set selection engine 82 optionally defined by the imaging facility processor or processors 12 to select a sub-set of the list mode data set 30 comprising list mode data contributing to image content of the region of interest in image space. For SPECT list mode data or non-time-of-flight PET imaging data, one approach for this selection is to include in the sub-set any line of response (LOR) that passes through the region of interest in image space, since such a LOR potentially contributes to the image content of the region of interest in image space. For time-of-flight (TOF) PET data, the time-of-flight localization along the LOF can be further used to select the sub-set, by choosing only those LORs that both pass through the region of interest in space and have time-of-flight localization within the region of interest. Other approaches can also be used to select the sub-set of the list mode data set 30 comprising list mode data contributing to image content of the region of interest in image space, such as approaches disclosed in Busch et al., WO 2007/100955 (published 7 Sep. 2007) which is incorporated herein by reference in its entirety. The imaging specialist then invokes the preprocessing (if selected) and the reconstruction engine 24 to generate an enhanced reconstructed image 84 that is stored in the one or more imaging facility memories 14. A copy of the enhanced reconstructed image 86 is forwarded to the oncology treatment planning facility and stored in the one or more oncology treatment planning facility memories 44 for review by the oncological specialist via the viewing station 46 of the oncology treatment planning facility.

At the imaging facility, some or all of the described manual re-reconstruction approach can be automated. For example, the selection of a rectangular containment box containing the region of interest in space selected by the oncology specialist is readily automated, and can optionally be followed by automated invocation of the region subset selection engine 82 to select the subset of the list mode data set 30 for reconstruction, optionally further followed by automatic invocation of the pre-processor if appropriate (for example, automatic invocation of the LMC engine 80 if requested in the re-reconstruction request) and optionally still further followed by automatic invocation of the reconstruction engine 24 to perform the re-reconstruction in accordance with the parameters of the re-reconstruction request. Automation of these operations advantageously reduces the amount of human time involved in servicing the re-reconstruction activities.

In the illustrated embodiments, the images 32, 84 are communicated electronically (for example, via the Internet or a local area network) from the imaging facility to the oncology treatment planning facility. However, it is also contemplated for these images to be transferred from the imaging facility to the oncology treatment planning facility in printed form, for example via an interdepartmental mail system or via the United States Postal Service or via an overnight express mail service.

In the embodiments described with reference to FIG. 1, the re-reconstruction process is performed in a manual, automated, or semi-automated fashion at the imaging facility. This approach advantageously leverages the existing image reconstruction components 24, 80, 82 of the imaging facility for performing the re-reconstruction. However, the approach of FIG. 1 entails transferring queued re-reconstruction requests to the imaging facility and transferring the enhanced reconstructed image 84 back to the oncological treatment planning facility. The approach of FIG. 1 also imposes additional re-reconstruction tasks onto the existing image reconstruction components 24, 80, 82. In some embodiments, processing of the re-reconstruction tasks are queued until low processing load times of the imaging facility. For example, the processing of the re-reconstruction tasks can optionally be queued during the day and performed overnight, when the imaging facility is not in use or is possibly handing a lower throughput of imaging subjects. For fully automated re-reconstruction, such queuing is straightforward. For semi-automated or manual re-reconstruction, queuing for overnight or other delayed processing can still be done by assigning the re-reconstruction requests a suitably low execution priority.

With reference to FIG. 2, in a variant approach the processing load is offloaded to the oncological treatment planning facility by providing a modified one or more oncology treatment planning processors 142 and modified one or more oncology treatment planning memories 144 (suitably embodied, for example, by one or more modified computers 145) that are modified to additionally define or embody a reconstruction engine 150, optional LMC engine 152, and optional region subset selection engine 154 at the oncological treatment planning facility. In some such embodiments, the corresponding LMC engine 80 and/or the corresponding and region subset selection engine 82 at the imaging facility are omitted, since these components are typically not used in performing the standard reconstruction. In embodiments comporting with FIG. 2, the copy of the standard whole body image 62 is still copied from the imaging facility to the oncology treatment planning facility, as is the CT image 60 if that image is generated at the imaging facility. Additionally, however, the list mode data set 30 is forwarded from the imaging facility to the oncology treatment planning facility, and the modified one or more oncology treatment planning memories 144 stores a copy of the list mode data set 160, so that the list mode data are available for the re-reconstruction processing locally at the oncology treatment planning facility. Alternatively, only the sub-set of the list mode data set 30 is transferred to the oncology treatment planning facility so as to provide sufficient list mode data for the local re-reconstruction processing. The interactive re-reconstruction configuration engine 70 operates as described respective to FIG. 1; but, in embodiments comporting with FIG. 2 the resulting re-reconstruction configuration is executed locally at the oncology treatment planning facility using the local reconstruction components 150, 152, 154.

Although the local reconstruction components 150, 152, 154 parallel the corresponding components 24, 80, 82 of the imaging facility, they are optionally different in function or capability. For example, in some contemplated embodiments, the reconstruction engine 24 of the imaging facility employs an iterative reconstruction algorithm such as ML-EM while the reconstruction engine 150 of the oncology treatment planning facility may employ an analytical reconstruction such as filtered backprojection. Alternatively, the imaging facility reconstruction processor 24 may employ an analytical reconstruction algorithm while the oncology treatment planning facility reconstruction processor 150 may employ an iterative reconstruction algorithm. Another contemplated difference is to employ conventional PET reconstruction in the reconstruction engine 24 to generate the standard whole volume image 32, and to employ time-of-flight localization in the reconstruction processor 150 to provide an enhanced image of the spatial region of interest. Further, because the re-reconstruction performed by the reconstruction engine 150 of the oncology treatment planning facility typically processes a smaller sub-set of the list mode data set 30, 160, the reconstruction engine 150 optionally also implements computationally intensive processing capabilities that are not usefully performed in the standard reconstruction of the complete list mode data set 30, 160. For example, the reconstruction engine 150 of the oncology treatment planning facility may optionally implement computationally intensive partial volume or PSF operations that are optionally not implemented in the reconstruction processor 24 of the imaging facility. Similarly, since the LMC and region subset selection that are typically used in the re-reconstruction but not in the initial standard reconstruction, the relevant components 80, 82 are optionally omitted at the imaging facility in embodiments comporting with FIG. 2.

Because the oncological specialist is not, in general, expert in the image reconstruction process, the local reconstruction components 150, 152, 154 are preferably configured to perform the re-reconstruction in an automated or semi-automated manner Optionally, the local reconstruction components 150, 152, 154 may provide dialog windows providing more advanced information to the oncological specialist, optionally with instructions to contact the imaging facility for further advice if and when attempting to implement more complex re-reconstruction processing.

Intensity modulated radiation therapy (IMRT) planning is used herein as an illustrative example. However, it will be appreciated that the disclosed techniques for enhanced list mode data set analysis based on re-reconstruction techniques is generally applicable to other types of radiation therapy planning, such as chemotherapy, brachytherapy, or so forth. In embodiments employing a therapy other than radiation therapy, the IMRT planning engine 54 is suitably replaced by another oncological treatment planning module that is configured to generate an oncological treatment plan employing the selected therapy modality. Furthermore, while application in oncology treatment planning is described herein as an illustrative example, the disclosed techniques of employing re-reconstruction of list mode data to provide an enhanced reconstructed image is more generally useful in any medical diagnostic or clinical application that employs a nuclear medical imaging instrument generating list mode data, such as a PET scanner, a gamma camera or SPECT instrument. For example, in cardiac imaging, and especially quantitative cardiac imaging, it is commonplace for a cardiac care center, cardiology department, or other cardiac treatment planning facility to order images acquired by PET, SPECT, or another imaging modality that generates list-mode imaging data. The cardiology specialist, upon review of the "standard" PET or SPECT images, may desire improved images that can be generated by re-reconstructing the list mode data or a portion thereof using something other than the standard reconstruction. For example, the cardiologist may want to employ local motion compensation, or may want to reconstruct a sub-set of the list mode data selected by retrospective cardiac gating, or so forth. The disclosed approaches can be readily adapted to facilitate re-reconstruction of list-mode data for such cardiology applications and others.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for reconstructing list mode data, the method comprising:
   reconstructing all list mode data of a list mode data set to generate a first reconstructed image;
   after the first reconstructed image is generated, identifying a region of interest in image space based on a feature delineated in the first reconstructed image and selecting a sub-set of the list mode data set comprising list mode data contributing to image content of the region of interest in image space; and
   reconstructing only the sub-set of the list mode data set utilizing a higher resolution reconstruction parameter than the reconstructing used to generate the first reconstructed image to generate an enhanced reconstructed image with higher resolution than the first reconstructed image.

2. The method as set forth in claim 1, wherein the reconstructing the sub-set further comprises:
   adjusting at least some list mode data of the sub-set to compensate for local motion; and
   reconstructing the adjusted sub-set to generate an enhanced reconstructed image including local motion compensation.

3. The method as set forth in claim 1, wherein the reconstructing the sub-set comprises:
   reconstructing using at least one of a partial volume correction and a system point spread function.

4. The method as set forth in claim 1, wherein the list mode data set comprises positron emission tomography (PET) list mode data, and the reconstructing to generate a first reconstructed image comprises:
   reconstructing all list mode data of the list mode data set to generate a first reconstructed image as a standard image comprising 4 mm$^3$ voxels.

5. The method as set forth in claim 1, wherein the reconstructing to generate a first reconstructed image is performed at an imaging facility and the selecting a sub-set is performed at a treatment planning facility.

6. The method as set forth in claim 5, wherein the reconstructing to generate an enhanced reconstructed image is performed at the treatment planning facility, and the method further comprises:

transferring at least the sub-set of the list mode data set from the imaging facility to the treatment planning facility.

7. The method as set forth in claim 5, wherein the reconstructing to generate an enhanced reconstructed image is performed at the imaging facility, and the method further comprises:
   generating identifying information sufficient for identifying the sub-set at the treatment planning facility;
   transferring the identifying information from the treatment planning facility to the imaging facility; and
   selecting the sub-set of the list mode data set at the imaging facility based on the identifying information.

8. The method as set forth in claim 7, wherein the identifying information includes at least one of (i) an identification of a region of interest in image space and (ii) an identification of an image resolution in image space.

9. The method as set forth in claim 1, further comprising:
   performing a quantitative diagnostic analysis on the enhanced reconstructed image.

10. The method as set forth in claim 9, wherein the quantitative diagnostic analysis comprises a standardized uptake value (SUV) analysis.

11. A method for reconstructing list mode data, the method comprising:
   reconstructing all list mode data of a list mode data set to generate a first reconstructed image, wherein the reconstructing to generate a first reconstructed image employs an iterative reconstruction algorithm;
   selecting a sub-set of the list mode data set; and
   reconstructing only the sub-set of the list mode data set to generate an enhanced reconstructed image, wherein the reconstructing to generate an enhanced reconstructed image employs a non-iterative reconstruction algorithm.

12. An image generation system comprising:
   a reconstruction module comprising a computer configured to perform a standard reconstruction of a list mode data set to generate a standard reconstructed image; and
   an oncology treatment planning module comprising a computer configured to generate a radiation therapy treatment plan, the oncology treatment planning module including at least a medical image viewing station and a re-reconstruction module configured to perform a reconstruction other than the standard reconstruction of at least a portion of the list mode data set to generate an enhanced reconstructed image;
   wherein the oncology treatment planning module includes the entire re-reconstruction module and does not include any portion of the reconstruction module.

13. The image generation system as set forth in claim 12, wherein:
   the reconstruction module employs a set of standard reconstruction parameters including at least a standard image resolution, and
   the re-reconstruction module includes an interactive re-reconstruction configuration engine enabling user selection of reconstruction parameters used in the re-reconstruction.

14. The image generation system as set forth in claim 13, wherein the interactive re-reconstruction configuration engine enables user selection of at least a region of interest in image space and the re-reconstruction module further comprises:
   a region subset selection engine that selects a subset of the list mode data set that contributes to image content of the region of interest in image space as the portion of the list mode data set that is reconstructed to generate the enhanced reconstructed image.

15. The image generation system as set forth in claim 12, wherein the oncology treatment planning module further comprises:
   an intensity-modulated radiation therapy (IMRT) planning engine configured to generate a radiation therapy session plan.

* * * * *